United States Patent
Kohr et al.

(10) Patent No.: US 10,548,848 B2
(45) Date of Patent: Feb. 4, 2020

(54) ALOGLIPTIN FORMULATION

(71) Applicant: Hexal Aktiengesellschaft, Holzkirchen (DE)

(72) Inventors: Thomas Kohr, Holzkirchen (DE); Christian Wawra, Holzkirchen (DE); Marco Marchesan, Holzkirchen (DE)

(73) Assignee: Hexal AG, Holzkirchen (DE)

( * ) Notice: Subject to any disclaimer, the term of this patent is extended or adjusted under 35 U.S.C. 154(b) by 1 day.

(21) Appl. No.: 15/736,592

(22) PCT Filed: Jun. 16, 2016

(86) PCT No.: PCT/EP2016/063969
§ 371 (c)(1),
(2) Date: Dec. 14, 2017

(87) PCT Pub. No.: WO2016/202961
PCT Pub. Date: Dec. 22, 2016

(65) Prior Publication Data
US 2018/0133160 A1 May 17, 2018

(30) Foreign Application Priority Data

Jun. 17, 2015 (EP) .................................. 15172512

(51) Int. Cl.
| | | |
|---|---|---|
| *A61K 9/28* | (2006.01) | |
| *A61K 9/16* | (2006.01) | |
| *A61K 31/513* | (2006.01) | |
| *A61K 31/155* | (2006.01) | |
| *A61K 31/4439* | (2006.01) | |

(52) U.S. Cl.
CPC .......... *A61K 9/2866* (2013.01); *A61K 9/1617* (2013.01); *A61K 9/1623* (2013.01); *A61K 9/1652* (2013.01); *A61K 9/1682* (2013.01); *A61K 31/155* (2013.01); *A61K 31/4439* (2013.01); *A61K 31/513* (2013.01)

(58) Field of Classification Search
None
See application file for complete search history.

(56) References Cited

U.S. PATENT DOCUMENTS

| | | | | |
|---|---|---|---|---|
| 2007/0066635 A1* | 3/2007 | Andres | ................ | A61K 31/513 514/269 |
| 2008/0107731 A1* | 5/2008 | Kohlrausch | .......... | A61K 9/2009 424/474 |
| 2010/0136127 A1 | 6/2010 | Yamamoto et al. | | |
| 2011/0206766 A1 | 8/2011 | Friedl et al. | | |
| 2011/0244040 A1 | 10/2011 | Ono et al. | | |
| 2012/0059011 A1* | 3/2012 | Birringer | ............... | A61K 31/44 514/249 |

FOREIGN PATENT DOCUMENTS

| | | |
|---|---|---|
| WO | 2005095381 A1 | 10/2005 |
| WO | 2007035372 A2 | 3/2007 |
| WO | 2008093878 A1 | 8/2008 |
| WO | 2010072680 A1 | 7/2010 |
| WO | 2010147768 A1 | 12/2010 |
| WO | 2014030051 A1 | 2/2014 |

OTHER PUBLICATIONS

H. Leonhard Ohrem, Eva Schornick, Adela Kalivoda & Roberto Ognibene. "Why is mannitol becoming more and more popular as a pharmaceutical excipient in solid". (Pharm. Dev. Technol., 2014; 19(3):257-262) (Year: 2014).*
European Pharmacopoeia (Ph. Eur.) 5.0-2.9.8.: Resistance to Crushing of Tablets.
European Pharmacopoeia (Ph. Eur.) 5.0-2.9.3.: Dissolution Test for Solid Dosage Forms.
European Pharmacopoeia (Ph. Eur.) 5.0-2.9.40.: Content Uniformity.

* cited by examiner

*Primary Examiner* — Michael P Cohen
(74) *Attorney, Agent, or Firm* — Luedeka Neely Group, P.C.

(57) ABSTRACT

The present invention belongs to the field of pharmaceutical industry and relates to a pharmaceutical composition comprising an intragranulate phase and an extragranulate phase, wherein the pharmaceutically active ingredient (API) 2-({6-[(3R)-3-aminopiperidin-1-yl]-3-methyl-2,4-dioxo-3,4-dihydropyrimidin-1(2H)-yl}methyl)benzonitrile or a pharmaceutically acceptable salt thereof, is present in the intragranulate phase, wherein said intragranulate phase is free from microcrystalline cellulose. Further, the present invention relates to a process for preparing the same.

9 Claims, 3 Drawing Sheets

Fig. 1 (Example 2):
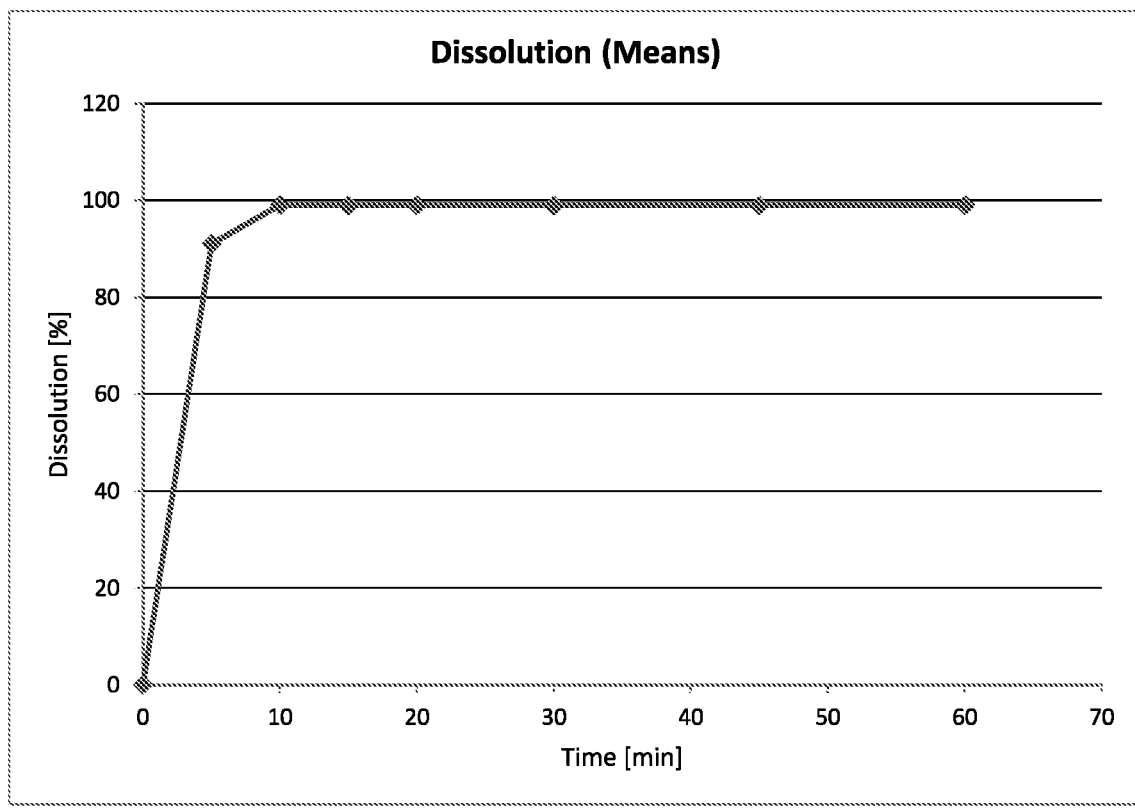

Fig. 2 (Example 3):
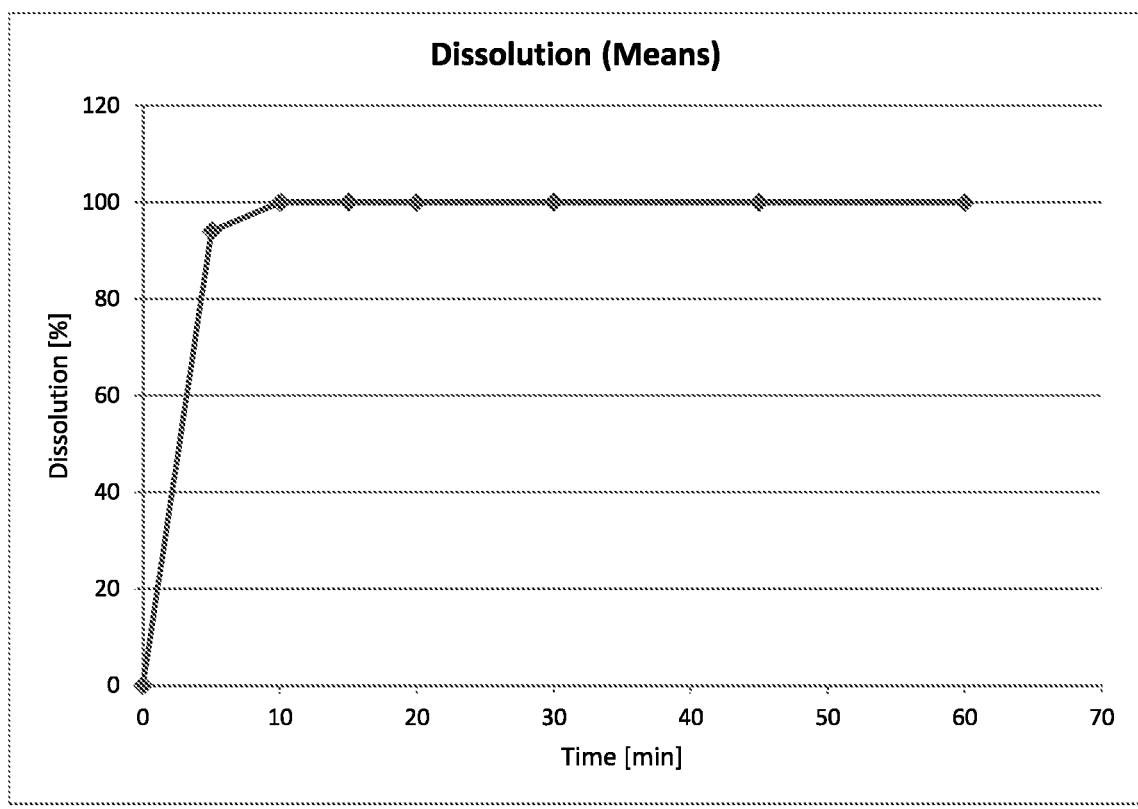

ALOGLIPTIN FORMULATION

This application is a Section 371 national phase entry of PCT application PCT/EP2016/063969, filed Jun. 16, 2016. This application also claims the benefit of the earlier filing date of European patent application 15172512.4, filed Jun. 17, 2015.

FIELD OF THE INVENTION

The present invention belongs to the field of pharmaceutical industry and relates to a pharmaceutical composition comprising the pharmaceutically active ingredient (API) 2-({6-[(3R)-3-aminopiperidin-1-yl]-3-methyl-2,4-dioxo-3,4-dihydropyrimidin-1(2H)-yl}methyl)benzonitrile (alogliptin) or a pharmaceutically acceptable salt thereof, to a pharmaceutical dosage form comprising or consisting of said pharmaceutical composition, to a granulate comprising said API, as well as to a process for preparing the same. Additionally, the present invention relates to a pharmaceutical composition, dosage form or tablet in a method of treating diabetes.

DESCRIPTION OF THE BACKGROUND ART

Only in very rare cases a pharmaceutically active ingredient (API) is prescribed or administered to a patient as such, i.e. without any excipients and additives, respectively. In the vast majority of cases APIs that are intended for being used to treat subjects suffering from a certain disease are present in a pharmaceutical composition, together with specific excipients, and are formulated into suitable dosage forms. The excipients are added in order to confer specific, desired properties to the pharmaceutical composition/dosage form comprising the API.

When choosing excipients, possible interactions between the API(s) and the excipient(s) that may have a negative influence on the performance or properties of the pharmaceutical composition or dosage form have to be taken into account. For instance, it may be that certain excipients, in combination with certain APIs, in particular APIs that easily induce tableting trouble, lead to troubles during formulating the respective dosage form such as a tablet ("tableting trouble"). These tableting troubles mainly occur during the production of the tablets, i.e. during the tableting step.

With this respect, various methods for avoiding or minimizing tableting trouble have been disclosed, for instance increasing the amount of magnesium stearate used as lubricant or elongating the mixing time of the various ingredients of the pharmaceutical composition and tablet, respectively.

Further with this respect, WO 2008/093878 A1 discloses a tablet comprising a granule and a tableting aid, wherein the granule comprises an API that easily induces tableting trouble and microcrystalline cellulose, and the tableting aid comprises magnesium stearate and microcrystalline cellulose.

However, increasing the amount of excipients (such as magnesium stearate) or elongating the mixing time may result in problems with regard to quality or impaired producibility. Additionally, the more excipients (in terms of amount) being present in a pharmaceutical composition or dosage form such as a tablet, the bigger in size the dosage form (e.g. tablet), while at the same time maintaining the API dose. This, in turn, results in a decreased patients' acceptance. If, on the other hand, the size of the dosage from is maintained, less API can be present in said dosage form. The amount of the respective excipients being present in a pharmaceutical composition, and resulting from this amount the size of said pharmaceutical composition/dosage form, is of particular interest if there is not only one API, but two or more APIs that are to be formulated into the pharmaceutical composition/dosage form. This is for instance the case with regard to combination preparations (i.e. preparations that contain more than one API), such as preparations that are used in the treatment of diabetes.

The possibility of splitting the amount of microcrystalline cellulose and manufacturing the resulting parts of microcrystalline cellulose in different phases of the pharmaceutical composition (e.g. one part in the intragranulate phase, one part in the extragranulate phase) is a complex process that is time-consuming and cost-intensive. Additionally, the batch-size determining step in the manufacture of pharmaceutical compositions comprising a granulate phase is the granulation step. Thus, the more excipients are present in the intragranulate phase, the smaller the size of the manufactured batch.

Therefore, there is a need for an improved pharmaceutical composition, in particular solid oral dosage form such as a tablet, comprising an API that easily induces tableting trouble, in particular alogliptin or a pharmaceutically acceptable salt thereof, and a process for preparing the same.

SUMMARY OF THE INVENTION

The present invention provides the following aspects, subject-matters and preferred embodiments, which respectively taken alone or in combination, further contribute to solving the object of the present invention:

(1) A pharmaceutical composition comprising an intragranulate phase and an extragranulate phase, wherein
   (i) said intragranulate phase comprises one or more pharmaceutically active ingredient(s) or salts thereof;
   (ii) one pharmaceutically active ingredient in the intragranulate phase is 2-({6-[(3R)-3-aminopiperidin-1-yl]-3-methyl-2,4-dioxo-3,4-dihydropyrimidin-1(2H)-yl}methyl)benzonitrile (alogliptin) or a pharmaceutically acceptable salt thereof;
   (iii) said intragranulate phase is free from microcrystalline cellulose; and
   (iv) said extragranulate phase comprises microcrystalline cellulose.

(2) The pharmaceutical composition according to item (1), wherein the pharmaceutically active ingredient in the intragranulate phase is alogliptin free base or alogliptin benzoate, preferably alogliptin monobenzoate.

(3) The pharmaceutical composition according to item (1) or (2), wherein the alogliptin monobenzoate is in the form of polymorphic form A or in amorphous form, and wherein the alogliptin free base is in the form of polymorphic form B, wherein said polymorphic form A is characterized by one or more physical properties selected from the group consisting of:
   an X-ray powder diffraction pattern using Cu-K$\alpha$ radiation with diffraction peaks at positions (° 2$\Theta$) as follows: 9.44, 10.84, 17.82, 18.75, 25.87, 28.52,
preferably with diffraction peaks at positions (° 2$\Theta$) as follows: 9.12, 9.44, 10.48, 10.84, 11.34, 12.49, 12.84, 14.09, 14.38, 14.90, 15.20, 16.83, 17.48, 17.82, 18.75, 20.09, 20.48, 20.64, 20.92, 21.18, 21.52, 21.82, 22.10, 22.88, 23.34, 23.64, 23.88, 24.22, 24.44, 25.87, 26.14, 27.02, 27.62, 28.09, 28.52, 29.06, 29.26, 29.74, 30.17, 31.66, 33.02, 34.34, 34.86, 35.12, 35.50, 36.07, 37.32, 37.52, 37.82, 38.02, 38.29, with +/−0.2 tolerance range of the respective 2Θ value;
an IR spectrum comprising absorption peaks at 1212, 1365, 1447, 1613 and 1697 cm$^{-1}$, preferably at 830, 876, 910, 950, 987, 1004, 1026, 1063, 1094, 1135, 1173, 1212, 1231, 1284, 1316, 1334, 1365, 1384, 1447, 1458, 1474, 1532, 1592, 1613, 1697, 2082, 2230, 2540, 2596, 2743, 2860, 2958, 2979 and 3085 cm$^{-1}$, with +/−2 cm$^{-1}$ tolerance range of the respective value;
an FT-Raman spectrum comprising peaks at 1065, 1103, 1235, 1288, 1337, 1365, 1624, 1689, 2883, 2983 and 3026 cm$^{-1}$, preferably at 825, 881, 910, 918, 987, 1003, 1027, 1039, 1065, 1084, 1103, 1135, 1157, 1167, 1172, 1184, 1206, 1235, 1288, 1337, 1365, 1385, 1417, 1446, 1461, 1474, 1557, 1577, 1597, 1624, 1652, 1689, 2230, 2860, 2883, 2957, 2970, 2983, 3026, 3053 and 3070 cm$^{-1}$, with +/−2 cm$^{-1}$ tolerance range of the respective value; and
a differential scanning calorimetry spectrum having an endotherm range at about 173° C. to about 195° C.;
and wherein said amorphous form is characterized by one or more physical properties selected from the group consisting of:
an X-ray powder diffraction pattern that shows a broad halo with no specific peaks present using Cu-Kα radiation;
an IR spectrum comprising absorption peaks at 1703, 1599, 1119, 868 and 809 cm$^{-1}$, preferably at 3062, 2949, 2861, 2571, 2225, 2136, 1703, 1652, 1599, 1541, 1440, 1375, 1286, 1228, 1172, 1134, 1119, 1084, 1068, 1024, 948, 868, 833 and 809 cm$^{-1}$;
an FT-Raman spectrum comprising peaks at 805, 1280 and 1703 cm$^{-1}$, preferably at 805, 834, 904, 1002, 1024, 1045, 1134, 1168, 1205, 1280, 1386, 1443, 1578, 1600, 1654, 1.703, 2225, 2864, 2958 and 3065 cm$^{-1}$; and
a differential scanning calorimetry spectrum having a $T_g$=70° C. (onset), an exotherm at 132° C., and an endotherm onset at 183° C.;
and wherein said polymorphic form B is characterized by one or more physical properties selected from the group consisting of:
an X-ray powder diffraction pattern using Cu-Kα radiation with diffraction peaks at positions (° 2Θ) as follows: 10.9, 12.5, 18.0, 19.0, 21.8,
with +/−0.2 tolerance range of the respective 2Θ value;
an IR spectrum comprising absorption peaks at 3358.7, 2223.7, 1642.2, 1433.4, 818.4 and 771.2 cm$^{-1}$, with +/−2 cm$^{-1}$ tolerance range of the respective value.
(4) The pharmaceutical composition according to any of items (1) to (3), wherein the amount of alogliptin or the pharmaceutically acceptable salt thereof in the intragranulate phase is in the range of from 3 to 50 wt.-%, preferably 5 to 35 wt.-%, more preferably 7 to 30 wt.-%, based on the total amount of ingredients of the intragranulate phase.
(5) The pharmaceutical composition according to item (4), wherein said pharmaceutical composition is a dosage form, preferably a tablet, wherein the amount of alogliptin free base in the intragranulate phase is 6.25 mg; 12.5 mg; or 25 mg per dosage form, or the amount of the pharmaceutically acceptable salt of alogliptin in the intragranulate phase is such that it corresponds to 6.25 mg, 12.5 mg, or 25 mg of alogliptin free base per dosage form, preferably the pharmaceutically acceptable salt of alogliptin is alogliptin monobenzoate and the amount thereof in the intragranulate phase is 8.5 mg, 17 mg or 34 mg alogliptin monobenzoate per dosage form.
(6) The pharmaceutical composition according to any of items (1) to (5), wherein the intragranulate phase further comprises one or more pharmaceutically acceptable excipients, selected from the group consisting of binders, diluents, surfactants, stabilizers, colorants, fluidizers, and pH adjusting agents, wherein said pharmaceutically acceptable excipients are not microcrystalline cellulose.
(7) The pharmaceutical composition according to item (6), wherein
the binder is selected from the group consisting of hydroxypropylmethylcellulose (HPMC), hydroxypropyl cellulose (HPC), povidone, copovidone (copolymers of vinylpyrrolidone with other vinylderivatives), methylcellulose, powdered acacia, gelatin, gum arabicum, guar gum, carbomer such as carbopol, and polymethacrylates, preferably the binder is HPC or povidone, more preferably the binder is HPC;
the diluent is selected from the group consisting of carbohydrates such as monosaccharides like glucose, oligosaccharides like sucrose and lactose (including anhydrous lactose and lactose monohydrate), starch such as maize starch, potato starch, rice starch and wheat starch, pregelatinized starch, calcium hydrogenphosphate, and sugar alcohols like sorbitol, mannitol, erythritol, and xylitol, a particularly preferred diluent is mannitol;
the surfactant is selected from the group consisting of sodium lauryl sulfate, polysorbate 80, and polyoxyethylene (160)polyoxypropylene(30)glycol;
the stabilizer is selected from the group consisting of tocopherol, tetrasodium edetate, nicotinamide, and cyclodextrins;
the colorant is selected from the group consisting of food colors such as Food Color Yellow No. 5, Food Color Red No. 2, Food Color Blue No. 2, food lake colors, red ferric oxide, and yellow ferric oxide;
the fluidizer is selected from the group consisting of light anhydrous silicic acid, hydrated silicon dioxide, and talc; and/or
the pH adjusting agent is selected from the group consisting of citrate, phosphate, carbonate, tartrate, fumarate, acetate, and amino acid salts, e.g. the sodium, potassium or calcium salts thereof;
wherein the pharmaceutically acceptable excipients are respectively different from each other.
(8) The pharmaceutical composition according to any of the preceding items, wherein the intragranulate phase in addition to the pharmaceutically active ingredient only comprises, as pharmaceutically acceptable excipient, a binder and/or a diluent, preferably both, a binder and a diluent, wherein the binder and/or the diluent are preferably selected from the group as defined in item (7), and wherein said pharmaceutically acceptable excipient is not microcrystalline cellulose.
(9) The pharmaceutical composition according to item (8), wherein the diluent is mannitol.
(10) The pharmaceutical composition according to item (8), wherein the binder is HPC, and/or the diluent is mannitol, preferably the binder is HPC and the diluent is mannitol.
(11) The pharmaceutical composition according to any of items (6) to (10), wherein the diluent represents 50 to 99 wt.-%, preferably 60 to 99 wt.-%, more preferably 65 to 90 wt.-% of the pharmaceutically acceptable excipients of the intragranulate phase.
(12) The pharmaceutical composition according to any of items (6) to (11), wherein the binder represents 2 to 8 wt.-%, preferably 3 to 6 wt.-%, more preferably 3 to 5 wt.-% of the pharmaceutically acceptable excipients of the intragranulate phase.

(13) The pharmaceutical composition according to any of the preceding items, wherein the extragranulate phase further comprises, in addition to the microcrystalline cellulose, pharmaceutically acceptable excipients selected from the group consisting of diluents, binders, surfactants, stabilizers, colorants, disintegrants, fluidizers, lubricants, glidants, and pH adjusting agents, wherein preferably
the diluent is selected from the group consisting of carbohydrates such as monosaccharides like glucose, oligosaccharides like sucrose and lactose (including anhydrous lactose and lactose monohydrate), starch such as maize starch, potato starch, rice starch and wheat starch, pregelatinized starch, calcium hydrogenphosphate, and sugar alcohols like sorbitol, mannitol, erythritol, and xylitol, a particularly preferred diluent is mannitol;
the binder is selected from the group consisting of hydroxypropylmethylcellulose (HPMC), hydroxypropyl cellulose (HPC), povidone, copovidone (copolymers of vinylpyrrolidone with other vinylderivatives), methylcellulose, powdered acacia, gelatin, gum arabicum, guar gum, carbomer such as carbopol, and polymethacrylates, preferably the binder is hydroxypropyl cellulose or povidone;
the surfactant is selected from the group consisting of sodium lauryl sulfate, polysorbate 80, and polyoxyethylene (160)polyoxypropylene(30)glycol;
the stabilizer is selected from the group consisting of tocopherol, tetrasodium edetate, nicotinamide, and cyclodextrins;
the colorant is selected from the group consisting of food colors such as Food Color Yellow No. 5, Food Color Red No. 2, Food Color Blue No. 2, food lake colors, red ferric oxide, and yellow ferric oxide;
the disintegrant is selected from the group consisting of carmellose (carboxymethyl cellulose), carmellose sodium, carmellose calcium, croscarmellose sodium (cellulose carboxymethylether sodium salt, crosslinked), croscarmellose calcium, starch, sodium starch glycolate, crospovidone (crosslinked polyvinyl pyrrolidone), and low-substituted hydroxypropylcellulose, particularly preferred disintegrants are selected from the group consisting of sodium starch glycolate, crospovidone and croscarmellose sodium, preferably the disintegrant is croscarmellose sodium or crospovidone, more preferably the disintegrant is croscarmellose sodium;
the fluidizer is selected from the group consisting of light anhydrous silicic acid, hydrated silicon dioxide, and talc;
the lubricant is selected from the group consisting of stearic acid, talc, sodium stearyl fumarate and magnesium stearate, a particularly preferred lubricant is magnesium stearate;
the glidant is selected from the group consisting of colloidal silica, hydrophobic colloidal silica and magnesium trisilicate, such as talc, particularly preferred glidants are selected from the group consisting of colloidal silica and hydrophobic colloidal silica; and/or
the pH adjusting agent is selected from the group consisting of citrate, phosphate, carbonate, tartrate, fumarate, acetate, and amino acid salts, e.g. the sodium, potassium or calcium salts thereof;
wherein the pharmaceutically acceptable excipients are respectively different from each other.
(14) The pharmaceutical composition according to any of the preceding items, wherein the extragranulate phase, in addition to microcrystalline cellulose, only contains, as pharmaceutically acceptable excipients, a lubricant and/or a disintegrant, preferably both, wherein the lubricant and/or the disintegrant are selected from the respective groups defined in item (13).
(15) The pharmaceutical composition according to item (14), wherein the lubricant is magnesium stearate, and the disintegrant is croscarmellose sodium.
(16) The pharmaceutical composition according to any of the preceding items, wherein the intragranulate phase, which does not contain microcrystalline cellulose, contains, as pharmaceutically acceptable excipients, mannitol and HPC, and wherein the extragranulate phase contains, in addition to microcrystalline cellulose, as pharmaceutically acceptable excipients, croscarmellose sodium and magnesium stearate.
(17) The pharmaceutical composition according to any of the preceding items, wherein the intragranulate phase contains, preferably consists of, alogliptin or its pharmaceutically acceptable salt as defined in any of items (2) to (5), mannitol and hydroxypropylcellulose, and wherein the extragranulate phase contains, preferably consists of, magnesium stearate, croscarmellose sodium, and microcrystalline cellulose.
(18) The pharmaceutical composition according to any of items (13) to (17), wherein the disintegrant represents 10 to 90 wt.-%, preferably 20 to 80 wt.-%, more preferably 20 to 40 wt.-%, even more preferably 20 to 30 wt.-% and most preferably 20 to 25 wt.-% of the pharmaceutically acceptable excipients of the extragranulate phase.
(19) The pharmaceutical composition according to any of items (13) to (18), wherein the lubricant represents 1 to 15 wt.-%, preferably 2 to 10 wt.-%, more preferably 4 to 8 wt.-% of the pharmaceutically acceptable excipients of the extragranulate phase.
(20) The pharmaceutical composition according to any of items (13) to (19), wherein the microcrystalline cellulose represents 40 to 90 wt.-%, preferably 55 to 85 wt.-%, more preferably 65 to 75 wt.-% of the pharmaceutically acceptable excipients of the extragranulate phase.
(21) The pharmaceutical composition according to any of the preceding items, wherein at least one further pharmaceutically active ingredient (API) or pharmaceutically acceptable salt thereof, in addition to alogliptin or its pharmaceutically acceptable salt, is present.
(22) The pharmaceutical composition according to item (21), wherein said further API is metformin or a pharmaceutically acceptable salt thereof and/or pioglitazone or a pharmaceutically acceptable salt thereof, preferably metformin hydrochloride and/or pioglitazone hydrochloride.
(23) The pharmaceutical composition according to any of items (21) to (22), wherein said further API or pharmaceutically acceptable salt thereof is present in the intragranulate phase, in the extragranulate phase, and/or in the coating if a coating is present, preferably said further API or pharmaceutically acceptable salt thereof is present in the intragranulate phase.
(24) The pharmaceutical composition according to item (23), wherein
the intragranulate phase contains alogliptin or its pharmaceutically acceptable salt as defined in any of items (2) to (5), preferably alogliptin monobenzoate as defined in any of items (2) to (5), metformin or its pharmaceutically acceptable salt, preferably metformin hydrochloride, mannitol, and povidone,
and wherein the extragranulate phase contains magnesium stearate, crospovidone, and microcrystalline cellulose.
(25) The pharmaceutical composition according to item (23), wherein the intragranulate phase contains alogliptin or its pharmaceutically acceptable salt as defined in any of items (2) to (5), preferably alogliptin monobenzoate as defined in any of items (2) to (5), pioglitazone or its pharmaceutically acceptable salt, preferably pioglitazone hydrochloride, mannitol, lactose monohydrate and hydroxypropylcellulose, and wherein the extragranulate phase contains magnesium stearate, croscarmellose sodium, and microcrystalline cellulose.

(26) The pharmaceutical composition according to any of items (21) to (25), wherein the only pharmaceutically active ingredients being present in the pharmaceutical composition are
alogliptin or a pharmaceutically acceptable salt thereof, preferably alogliptin monobenzoate; and
metformin or a pharmaceutically acceptable salt thereof, or pioglitazone or a pharmaceutically acceptable salt thereof, preferably metformin hydrochloride or pioglitazone hydrochloride.

(27) The pharmaceutical composition according to item (26), wherein the only pharmaceutically active ingredients being present in the pharmaceutical composition are
alogliptin monobenzoate; and
metformin hydrochloride or pioglitazone hydrochloride.

(28) The pharmaceutical composition according to any of the preceding items, wherein said pharmaceutical composition comprises a coating, preferably the coating comprises hypromellose (hydroxypropyl methyl cellulose), titanium dioxide and iron oxide.

(29) The pharmaceutical composition according to item (28), wherein the coating additionally comprises polyethylene glycol and/or talc, preferably polyethylene glycol, more preferably polyethylene glycol 6000 or polyethylene glycol 8000 (Macrogol 6000 or Macrogol 8000).

(30) The pharmaceutical composition according to any of the preceding items, wherein the weight percentage of the intragranulate phase is in the range of from 65 to 95 wt.-%, preferably 75 to 85 wt.-%, more preferably 75 to 80 wt.-%, based on the combined total weight of the intragranulate phase and extragranulate phase excluding the coating, if present.

(31) A pharmaceutical dosage form, comprising or consisting of the pharmaceutical composition as defined in any of the preceding items.

(32) The pharmaceutical dosage form according to item (31), wherein said dosage form is a solid oral dosage form, such as a tablet (including a tablet to be swallowed, an orally disintegrating tablet, an effervescent tablet, a chewable tablet, a lozenge) or a capsule filled with mini-tablets, preferably said solid oral dosage form is a tablet, more preferably the tablet is a coated tablet or an uncoated tablet.

(33) The pharmaceutical dosage form according to item (32), wherein said dosage form is an uncoated tablet, wherein the hardness of said tablet is in a range of from about 60 to about 150 N, preferably the hardness is in a range of from about 60 to about 120 N, more preferably the hardness is in a range of from about 60 to 100 N, even more preferably the hardness is in a range of from about 70 to 90 N, measured according to the European Pharmacopoeia 5.0 2.9.8 with the apparatus Schleuniger Typ 6D 4.11/6D 4.50, wherein the tablets are placed between the jaws in a manner that the force applies to the longest axis of the tablets, where applicable.

(34) The tablet according to any of items (31) to (33), wherein not less than 92%, preferably not less than 93%, even more preferably not less than 94% of the alogliptin or pharmaceutically acceptable salt thereof is dissolved out in 5 min., and/or not less than 99.5%, preferably not less than 100%, of the alogliptin or pharmaceutically acceptable salt thereof is dissolved out in 10 min., when the tablet is subjected to a dissolution test according to the Paddle method described in the European Pharmacopoeia 5.0 2.9.3 in a test volume of 900 ml in the test medium 0.01 M HCl at a stirring speed of 50 rpm using a Sotax AP 825 device with a photometer (wavelength 228 nm).

(35) The tablet according to any of items (32) to (34), wherein said tablet has an oval, biconvex form.

(36) The tablet according to item (35), wherein said tablet has a length of 8 to 12 mm, preferably 9 to 11 mm, a width of 4 to 7 mm, preferably 5 to 6 mm, and a height of 3 to 6 mm, preferably 3 to 4 mm.

(37) The tablet according to any of items (32) to (36), wherein said tablet has a breaking notch and/or embossment.

(38) The tablet according to item (37), wherein said breaking notch is present on one side of the tablet or on both sides of the tablet, preferably on one side of the tablet, and/or said embossment is present on one side of the tablet or on both sides of the tablet, preferably on one side of the tablet.

(39) A process for preparing a pharmaceutical composition comprising an intragranulate phase and an extragranulate phase, comprising the steps of
(a) providing an intragranulate phase comprising one or more pharmaceutically active ingredient(s), wherein one pharmaceutically active ingredient is 2-({6-[(3R)-3-aminopiperidin-1-yl]-3-methyl-2,4-dioxo-3,4-dihydropyrimidin-1(2H)-yl}methyl)benzonitrile (alogliptin) or a pharmaceutically acceptable salt thereof, and wherein said intragranulate phase is free from microcrystalline cellulose;
(b) providing an extragranulate phase comprising microcrystalline cellulose;
(c) mixing the intragranulate phase from step (a) with the extragranulate phase from step (b) in order to obtain a pharmaceutical composition comprising an intragranulate phase and an extragranulate phase.

(40) The process according to item (39), wherein the alogliptin or the pharmaceutically acceptable salt thereof being present in the intragranulate phase is as defined in any of items (2) to (5), and/or wherein the intragranulate phase further comprises one or more pharmaceutically acceptable excipients, selected from the group as defined in any of items (6) to (12), and wherein said pharmaceutically acceptable excipients are not microcrystalline cellulose.

(41) The process according to item (39) or (40), wherein step (a) comprises a wet granulation step or a dry granulation step, preferably a wet granulation step, more preferably a fluidized bed granulation step.

(42) The process according to any of items (39) to (40), wherein step (a) comprises
(a-1) uniformly mixing the one or more pharmaceutically active ingredient(s) and, if present, the one or more pharmaceutically acceptable excipient(s), thereby obtaining a mixture, and
(a-2) granulating the mixture obtained in step (a-1), preferably by using an aqueous granulation liquid, more preferably by spraying an aqueous solution of hydroxypropylcellulose, thereby obtaining a granulate,
(a-3) drying the granulate obtained in step (a-2), and
(a-4) pulverizing the granulate and sieving the pulverized granulate, thereby obtaining sized granulate.

(43) The process according to any of items (39) to (42), wherein the extragranulate phase of step (b) in addition to the microcrystalline cellulose further comprises pharmaceutically acceptable excipients as defined in any of items (13) to (15).

(44) The process according to any of items (39) to (43), wherein in step (c) the extragranulate phase is added to the intragranulate phase obtained after step (a).

(45) The process according to any of items (39) to (44), wherein step (c) is carried out by using a tumbler mixer.
(46) The process according to any of items (39) to (45), comprising a further step (d) of formulating the pharmaceutical composition obtained after step (c), comprising an intragranulate phase and an extragranulate phase, into a dosage form, preferably into a solid oral dosage form.
(47) The process according to item (46), wherein the solid oral dosage form is a tablet (including a tablet to be swallowed, an orally disintegrating tablet, an effervescent tablet, a chewable tablet, a lozenge) or a capsule filled with mini-tablets, preferably said composition is a tablet.
(48) The process according to item (46) or (47), wherein step (d) involves a compression step.
(49) The process according to any of items (39) to (48), wherein the mixing in step (c) is carried out over a time period being in the range of from about 5 min. to 30 min., preferably from about 10 min. to 20 min.
(50) A granulate comprising one or more pharmaceutically active ingredient(s), wherein one pharmaceutically active ingredient is 2-({6-[(3R)-3-aminopiperidin-1-yl]-3-methyl-2,4-dioxo-3,4-dihydropyrimidin-1(2H)-yl}methyl)benzonitrile (alogliptin) or a pharmaceutically acceptable salt thereof, and wherein said granulate is free from microcrystalline cellulose.
(51) The granulate according to item (50), wherein the amount of alogliptin or its pharmaceutically acceptable salt in the granulate is in the range of from 3 to 50 wt.-%, preferably 5 to 35 wt.-%, more preferably 7 to 30 wt.-%, based on the total amount of ingredients of the granulate.
(52) The granulate according to item (50) or (51), wherein alogliptin and the pharmaceutically acceptable salt thereof are as defined in any of items (2) to (5).
(53) The granulate according to any of items (50) to (52), further comprising metformin or a pharmaceutically acceptable salt thereof and/or pioglitazone or a pharmaceutically acceptable salt thereof, preferably metformin hydrochloride and/or pioglitazone hydrochloride.
(54) The granulate according to any of items (50) to (53), further comprising mannitol and one or more excipients being different from mannitol, selected from the group consisting of binders, diluents, surfactants, stabilizers, colorants, fluidizers, and pH adjusting agents, wherein the pharmaceutically acceptable excipients are not microcrystalline cellulose.
(55) The granulate according to item (54), wherein the one or more excipient(s) are as defined in any of items (6) to (12).
(56) A process for preparing a granulate as defined in any of items (50) to (55), wherein said process comprises a granulation step.
(57) The process according to item (56), wherein the granulation step is as defined in item (41) or (42).
(58) The pharmaceutical composition of any of items (1) to (30), a pharmaceutical dosage form according to any of items (31) to (33), a tablet according to any of items (34) to (38), or a granulate according to any of items (50) to (55), for use in a method of treating diabetes, preferably type 2 diabetes.
(59) A pharmaceutical composition, obtained by applying a process as defined in any of items (39) to (49).
(60) The pharmaceutical composition according to item (59), wherein this composition is a solid oral dosage form, such as a tablet (including a tablet to be swallowed, an orally disintegrating tablet, an effervescent tablet, a chewable tablet, a lozenge) or a capsule filled with mini-tablets, preferably said solid oral dosage form is a tablet.

DETAILED DESCRIPTION OF THE INVENTION

The present invention is now described in more detail by preferred embodiments and examples, which are however presented for illustrative purpose only and shall not be understood as limiting the scope of the present invention in any way.

It was surprisingly found that by providing a pharmaceutical composition according to the present invention, in particular by providing a pharmaceutical composition comprising an intragranulate phase comprising an API that easily induces tableting trouble, such as alogliptin or a pharmaceutically acceptable salt thereof, and being free from microcrystalline cellulose, and further comprising an extragranulate phase comprising microcrystalline cellulose (MC), the occurrence of tableting trouble can be avoided. This was unexpected, since it was known in prior art that the presence of microcrystalline cellulose in both, the granulate phase and the extragranulate phase, provides for pharmaceutical compositions not exhibiting tableting troubles.

Consequently, it was surprising that a pharmaceutical composition not comprising microcrystalline cellulose in the intragranulate phase, but only in the extragranulate phase, does not exhibit tableting trouble. Without wishing to be bound by any theory, it is presently assumed that the superior properties of microcrystalline cellulose for instance with regard to compressibility, binding capacity, and comparably low friability, in combination with an API easily inducing tableting trouble, and with this microcrystalline cellulose only being present in the extragranulate phase but not in the intragranulate phase of a pharmaceutical composition, results in pharmaceutical compositions that do not exhibit tableting trouble.

Accordingly, the pharmaceutical composition according to the present invention represents a pharmaceutical composition that exhibits essentially no, preferably no, tableting trouble, wherein microcrystalline cellulose is not present in the intragranulate phase, with a consequential significant benefit that API load can be substantially increased, yet without tableting troubles despite of the API being one that easily induces tableting troubles. In addition, as microcrystalline cellulose is omitted in the intragranulate phase, the resulting dosage form can have a smaller size compared to dosage forms that have microcrystalline cellulose present in the intragranulate and extragranulate phase. This results in an improved acceptance in particular by elderly people or children. The smaller the size of an oral dosage form such as a tablet, the better is the patients' acceptance, as it can for instance be easier swallowed. It is also possible that the size is comparable with the size of tablets having MC in the intragranulate and extragranulate phase, however that instead of the microcrystalline cellulose more API is present in the intragranulate phase. Moreover, as microcrystalline cellulose is not present in the intragranulate phase, there is no contact between this excipient and the API and thus potentially damaging interactions between microcrystalline cellulose and API can be avoided.

Further, according to the present invention it is not necessary any more to split up the amount of MC in order to be present in the intragranulate phase as well as in the extragranulate phase. Therefore, the manufacturing process is simplified. Additionally, as it is in general the granulation step that is determining the size of the respective production batch, by omitting the MC in the intragranulate phase the batch size can be increased.

Moreover, the present invention also provides for a pharmaceutical composition and a process for preparing the same, wherein the obtained composition exhibits essentially no (or no) tableting trouble, even if the pharmaceutical composition (such as tablet) comprises surface markers such as a breaking notch and/or an embossment.

Thus, the present invention relates to a pharmaceutical composition comprising an intragranulate phase and an extragranulate phase. Said intragranulate phase (features (i) to (iii) of item 1) comprises an API that easily induces tableting trouble or a pharmaceutically acceptable salt thereof, and is free from microcrystalline cellulose. The extragranulate phase (feature (iv) of item 1) comprises microcrystalline cellulose.

Whenever it is disclosed herein that there is no MC present in the intragranulate phase of the pharmaceutical composition, it has to be noted that it is not excluded that MC is present in a potential layer or coating that may applied on the pharmaceutical composition in a later stage.

Within the meaning of the present invention, the term "intragranulate phase" denotes a part of a pharmaceutical composition that is obtained by granulating a starting material (i.e. the API(s) and the pharmaceutically acceptable excipients listed with regard to the intragranulate phase). This granulation step can for instance be a wet or dry granulation step, preferably it is a wet granulation step, even more preferably a fluidized bed granulation step.

Within the meaning of the present invention, the term "extragranulate phase" denotes the part of a pharmaceutical composition that is mixed with the intragranulate phase to obtain a pharmaceutical composition. The extragranulate phase does not comprise a coating that may be present on the final dosage form.

The intragranulate phase has been subjected to a granulation process. Whether or not a defined phase (compartment) of the pharmaceutical composition has been subjected to a granulation process (or not) can be assessed by a person skilled in the art by using suitable routine methods that are commonly known in the art. Examples of such methods are for instance imaging techniques, e.g. electron microscopy, or Raman spectroscopy.

In general, granulation denotes a process of collecting particles together by creating bonds between them, resulting in the formation of granules. "Granulation" can be a wet granulation or a dry granulation process. Thus, the granulation process can comprise any suitable granulation step such as a wet granulation step (high shear granulation, low shear granulation, fluidized bed granulation) or a dry granulation step. These types of granulation processes are known to a person skilled in the art and are carried out in the present invention according to suitable, commonly known protocols.

The term "wet granulation" denotes a process typically comprising the provision of a granulation liquid and a starting material which comprises the API of the present invention. In any granulation process, the starting material can be powder, bulk, solution, molten liquid and the like. The granulation liquid is brought into contact with the starting material, which can be under influence of an impeller (as it is the case in a high shear granulator) or a low speed planetary mixer or trough mixer (as it is the case in a low shear wet granulation process), screws (as it is the case in a twin screw granulator) or air (as it is the case in a fluidized bed granulator), and granulating it. The granulation liquid can be either aqueous based or solvent based, e.g. based on water, acetone, ethyl alcohol, polyalcohol, and mixture thereof at an appropriate ratio. In a preferred embodiment of the present invention, the granulation liquid is aqueous based, preferably the granulation liquid is water. The obtained granules are dried, and the obtained granulated product (intragranulate phase) is subjected to a sizing process in order to give a sized product.

In a preferred embodiment, the wet granulation process applied in the present invention is a fluidized bed granulation process.

The term "dry granulation" denotes a granulation process that is used to form granules without using a liquid solution because the product to be granulated may be sensitive to moisture or heat. In order to form granules without the use of moisture or liquids, compacting and densifying the starting material is required. In the dry granulation process, primary powder particles are aggregated under high pressure. Typically, dry granulation can be conducted on a tablet press using slugging tooling, thereby producing a comparable large tablet, or on a roller compactor commonly referred to as chilsonator. The roller compactor has an auger-feed system that consistently delivers starting material (powder) uniformly between two pressure rollers. The powder is compacted into a ribbon or small pellet, passed through a mill and final blend, and can be followed by tablet compression.

The intragranulate phase comprises granules (granulate), which, in turn, comprise at least one API that easily induces tableting trouble. Within the meaning of the present invention, the term "tableting trouble" denotes unwanted events that occur during tableting. Such unwanted events include sticking (attachment of starting material, e.g. powder, to punch), binding (increased friction between die and tablet), capping (cap-like detachment of the produced tablet), laminating (layer-like detachment of the produced tablet), and the like. In particular, the present invention addresses the tableting troubles sticking to the tablet punches, and capping. Usually, as soon as during the manufacture of a tablet tableting troubles occur, the tableting process is stopped. Hence, within the meaning of the present invention, the term "severe tableting troubles" denotes that within a time period of 2 min. after starting the tableting process tableting trouble occurs, e.g. sticking, binding, capping, and/or laminating.

Further, within the meaning of the present invention the term "tableting troubles" denotes that within a time period of more than 2 min. and up to 10 min. tableting trouble as defined above occurs. Finally, within the meaning of the present invention the term "no tableting troubles" denotes that during the whole tableting process no tableting troubles at all occur.

Within the meaning of the present invention, the tableting process comprises the stages of filling, compression and ejection of the tablet. The stages of filling, compression and ejection can be as follows:

The tableting process starts with the filling stage: The material to be tableted (e.g. the mixture to be tableted, comprising the intragranulate phase and the extragranulate phase) is filled into the bore of the die of the tableting machine and the material to be tableted is leveled, in order to ensure that the bore is filled with an exact volume of material to be tableted.

Then, after completion of the filling stage, the compression stage begins. In this stage, the material to be compressed is first pre-compressed in order to remove excess air. Then, the material to be tableted is fully compressed until the predetermined correct pressure is reached. Then, the upper punch is lifted out of the way, enabling the ejection of the thus-obtained tablet.

The final stage of tableting process is the ejection of the tablet.

The APIs easily inducing such tableting trouble are known to a person skilled in the art and are APIs that induce the above listed unwanted events during tableting. Examples of such APIs include the compounds listed in US 2005/0261271, preferably 2-({6-[(3R)-3-aminopiperidin-1-yl]-3-methyl-2,4-dioxo-3,4-dihydropyrimidin-1(2H)-yl}methyl) benzonitrile (also referred to as alogliptin) or a pharmaceutically acceptable salt thereof, ibuprofen, vitamin C, trimebutine maleate, and the like, in particular alogliptin or a pharmaceutically acceptable salt thereof.

In a most preferred embodiment where the concept of the present invention is particularly useful, one of the API(s) that is (are) present in the intragranulate phase of the pharmaceutical composition is alogliptin or a pharmaceutically salt thereof, more preferably alogliptin free base or alogliptin benzoate, more preferably alogliptin monobenzoate. Alogliptin and its pharmaceutically acceptable salts are known e.g. from WO 2005/095381.

In a further preferred embodiment, the alogliptin monobenzoate is in the form of polymorphic form A or in amorphous form, and the alogliptin free base is in the form of polymorph B (polymorphic form B).

Polymorphic form A of alogliptin monobenzoate corresponds to form A as disclosed in WO 2007/035372 and is characterized by one or more physical properties selected from the group consisting of:

an X-ray powder diffraction pattern using Cu-Kα radiation with diffraction peaks at positions (° 2Θ) as follows: 9.44, 10.84, 17.82, 18.75, 25.87, 28.52, preferably with diffraction peaks at positions (° 2Θ) as follows: 9.12, 9.44, 10.48, 10.84, 11.34, 12.49, 12.84, 14.09, 14.38, 14.90, 15.20, 16.83, 17.48, 17.82, 18.75, 20.09, 20.48, 20.64, 20.92, 21.18, 21.52, 21.82, 22.10, 22.88, 23.34, 23.64, 23.88, 24.22, 24.44, 25.87, 26.14, 27.02, 27.62, 28.09, 28.52, 29.06, 29.26, 29.74, 30.17, 31.66, 33.02, 34.34, 34.86, 35.12, 35.50, 36.07, 37.32, 37.52, 37.82, 38.02, 38.29,
with +/−0.2 tolerance range of the respective 2Θ value, more preferably with diffraction peaks at positions (° 2Θ) and relative intensities (I/I$_0$) as follows:

| Peaks positions (°2Θ) | Relative intensities (I/I$_0$) |
|---|---|
| 9.44 | 56 |
| 10.84 | 28 |
| 17.82 | 50 |
| 18.75 | 100 |
| 25.87 | 16 |
| 28.52 | 25 | with +/−0.2 tolerance range of the respective 2Θ value, even more preferably with diffraction peaks at positions (° 2Θ) and relative intensities (I/I$_0$) as follows:

| Peaks positions (°2Θ) | Relative intensities (I/I$_0$) |
|---|---|
| 9.12 | 7 |
| 9.44 | 56 |
| 10.48 | 3 |
| 10.84 | 28 |
| 11.34 | 10 |
| 12.49 | 8 |
| 12.84 | 3 |
| 14.09 | 7 |
| 14.38 | 5 |
| 14.90 | 10 |
| 15.20 | 27 |
| 16.83 | 3 |
| 17.48 | 4 |
| 17.82 | 50 |
| 18.75 | 100 |
| 20.09 | 21 |
| 20.48 | 5 |
| 20.64 | 20 |
| 20.92 | 83 |
| 21.18 | 51 |
| 21.52 | 17 |
| 21.82 | 34 |
| 22.10 | 14 |
| 22.88 | 9 |
| 23.34 | 11 |
| 23.64 | 20 |
| 23.88 | 9 |
| 24.22 | 7 |
| 24.44 | 12 |
| 25.87 | 16 |
| 26.14 | 4 |
| 27.02 | 28 |
| 27.62 | 16 |
| 28.09 | 13 |
| 28.52 | 25 |
| 29.06 | 14 |
| 29.26 | 9 |
| 29.74 | 8 |
| 30.17 | 3 |
| 31.66 | 4 |
| 33.02 | 3 |
| 34.34 | 12 |
| 34.86 | 7 |
| 35.12 | 11 |
| 35.50 | 8 |
| 36.07 | 8 |
| 37.32 | 3 |
| 37.52 | 4 |
| 37.82 | 9 |
| 38.02 | 9 |
| 38.29 | 15 | with +1-0.2 tolerance range of the respective 2Θ value;

an IR spectrum comprising absorption peaks at 1212, 1365, 1447, 1613 and 1697 cm$^{-1}$, preferably at 830, 876, 910, 950, 987, 1004, 1026, 1063, 1094, 1135, 1173, 1212, 1231, 1284, 1316, 1334, 1365, 1384, 1447, 1458, 1474, 1532, 1592, 1613, 1697, 2082, 2230, 2540, 2596, 2743, 2860, 2958, 2979 and 3085 cm$^{-1}$, with +/−2 cm$^{-1}$ tolerance range of the respective value;

an FT-Raman spectrum comprising peaks at 1065, 1103, 1235, 1288, 1337, 1365, 1624, 1689, 2883, 2983 and 3026 cm$^{-1}$, preferably at 825, 881, 910, 918, 987, 1003, 1027, 1039, 1065, 1084, 1103, 1135, 1157, 1167, 1172, 1184, 1206, 1235, 1288, 1337, 1365, 1385, 1417, 1446, 1461, 1474, 1557, 1577, 1597, 1624, 1652, 1689, 2230, 2860, 2883, 2957, 2970, 2983, 3026, 3053 and 3070 cm$^{-1}$, with +/−2 cm$^{-1}$ tolerance range of the respective value; and a differential scanning calorimetry spectrum having an endotherm range at about 173° C. to about 195° C.

The amorphous form of alogliptin monobenzoate corresponds to amorphous form 1 as disclosed in WO 2007/035372 and is characterized by one or more physical properties selected from the group consisting of:

an X-ray powder diffraction pattern that shows a broad halo with no specific peaks present using Cu-Kα radiation;

an IR spectrum comprising absorption peaks at 1703, 1599, 1119, 868 and 809 cm$^{-1}$, preferably at 3062, 2949, 2861, 2571, 2225, 2136, 1703, 1652, 1599, 1541, 1440, 1375, 1286, 1228, 1172, 1134, 1119, 1084, 1068, 1024, 948, 868, 833 and 809 cm$^{-1}$;

an FT-Raman spectrum comprising peaks at 805, 1280 and 1703 cm$^{-1}$, preferably at 805, 834, 904, 1002, 1024, 1045, 1134, 1168, 1205, 1280, 1386, 1443, 1578, 1600, 1654, 1703, 2225, 2864, 2958 and 3065 cm$^{-1}$; and a differential scanning calorimetry spectrum having a $T_g$=70° C. (onset), an exotherm at 132° C., and an endotherm onset at 183° C.

The polymorphic form B of alogliptin free base corresponds to the crystalline form of alogliptin free base as disclosed in WO 2010/072680 and is characterized by one or more physical properties selected from the group consisting of:

an X-ray powder diffraction pattern using Cu-Kα radiation with diffraction peaks at positions (02θ) as follows: 10.9, 12.5, 18.0, 19.0, 21.8, with +/−0.2 tolerance range of the respective 2Θ value;
an IR spectrum comprising absorption peaks at 3358.7, 2223.7, 1642.2, 1433.4, 818.4 and 771.2 cm$^{-1}$, with +/−2 cm$^{-1}$ tolerance range of the respective value. Preferably, the polymorphic form B is an anhydrous form containing less than 1.6% of water when stored at 25° C. and 90% relative humidity.

The amount of the API inducing tableting trouble, preferably alogliptin or a pharmaceutically acceptable salt thereof, is present in the intragranulate phase in a range of from 3 to 50 wt.-%, preferably 5 to 35 wt.-%, more preferably 7 to 30 wt.-%, based on the total amount of ingredients of the intragranulate phase.

If the pharmaceutical composition according to the present invention is a dosage form as defined herein, preferably a tablet, the amount of alogliptin free base in the intragranulate phase is 6.25 mg; 12.5 mg; or 25 mg per dosage form, or the amount of the pharmaceutically acceptable salt of alogliptin in the intragranulate phase is such that it corresponds to 6.25 mg, 12.5 mg, or 25 mg of alogliptin free base per dosage form, preferably the pharmaceutically acceptable salt of alogliptin is alogliptin monobenzoate and the amount thereof in the intragranulate phase is 8.5 mg, 17 mg or 34 mg alogliptin monobenzoate per dosage form.

The intragranulate phase of the pharmaceutical composition may further contain excipients (i.e. ingredients in a pharmaceutical composition that are not the active ingredient) that are usually used in the field of pharmaceutical preparation. The choice of the excipients will depend on various factors such as how the granulate phase is manufactured (e.g. wet granulation such as low shear granulation, high shear granulation, fluid bed granulation; dry granulation), or the desired release profile (e.g. fast/slow release; release of the API(s) at different pH values, or at different time points after intake).

Typically, a wet granulated pharmaceutical composition (which in the present invention is represented by the intragranulate phase if this intragranulate phase was prepared by wet granulation) contains excipients such as binders, diluents, surfactants, stabilizers, colorants, fluidizers, and pH adjusting agents, wherein said pharmaceutically acceptable excipients are not microcrystalline cellulose. Examples for the above-listed excipients are known to a skilled person.

In a preferred embodiment, the binder is selected from the group consisting of hydroxypropylmethylcellulose (HPMC), hydroxypropyl cellulose (HPC), povidone, copovidone (copolymers of vinylpyrrolidone with other vinylderivatives), methylcellulose, powdered acacia, gelatin, gum arabicum, guar gum, carbomer such as carbopol, and polymethacrylates, preferably the binder is HPC or povidone, more preferably the binder is HPC;

the diluent is selected from the group consisting of carbohydrates such as monosaccharides like glucose, oligosaccharides like sucrose and lactose (including anhydrous lactose and lactose monohydrate), starch such as maize starch, potato starch, rice starch and wheat starch, pregelatinized starch, calcium hydrogenphosphate, and sugar alcohols like sorbitol, mannitol, erythritol, and xylitol, a particularly preferred diluent is mannitol;

the surfactant is selected from the group consisting of sodium lauryl sulfate, polysorbate 80, and polyoxyethylene (160)polyoxypropylene(30)glycol;

the stabilizer is selected from the group consisting of tocopherol, tetrasodium edetate, nicotinamide, and cyclodextrins;

the colorant is selected from the group consisting of food colors such as Food Color Yellow No. 5, Food Color Red No. 2, Food Color Blue No. 2, food lake colors, red ferric oxide, and yellow ferric oxide;

the fluidizer is selected from the group consisting of light anhydrous silicic acid, hydrated silicon dioxide, and talc; and/or the pH adjusting agent is selected from the group consisting of citrate, phosphate, carbonate, tartrate, fumarate, acetate, and amino acid salts, e.g. the sodium, potassium or calcium salts thereof;

wherein the pharmaceutically acceptable excipients are respectively different from each other. In an even more preferred embodiment, the intragranulate phase in addition to the pharmaceutically active ingredient only comprises, as pharmaceutically acceptable excipient, a binder and/or a diluent, preferably both, a binder and a diluent, wherein the binder and/or diluent are preferably selected from the group as defined above, preferably the binder is HPC and/or the diluent is mannitol, and wherein said pharmaceutically acceptable excipient is not microcrystalline cellulose. Even more preferred, the pharmaceutical composition contains an intragranulate phase, with this intragranulate phase only comprising, as pharmaceutically acceptable excipients, HPC as binder and mannitol as diluent.

Preferably, the diluent represents 50 to 99 wt.-%, preferably 60 to 99 wt.-%, more preferably 65 to 90 wt.-% of the pharmaceutically acceptable excipients of the intragranulate phase, and/or the binder represents 2 to 8 wt.-%, preferably 3 to 6 wt.-%, more preferably 3 to 5 wt.-% of the pharmaceutically acceptable excipients of the intragranulate phase.

It has now surprisingly been found in the present invention that the excipient MC, which confers various advantageous properties to the pharmaceutical composition and dosage form, respectively, can be omitted in the intragranulate phase, while however at the same time the pharmaceutical composition and dosage form, respectively, still exhibits the desired properties e.g. with regard to manufacturability (occurrence of tableting troubles can be avoided, even if the tablets are produced with a breaking notch and/or an embossment), tablet hardness (resistance to crushing), dissolution profile, and content uniformity.

Additionally, it is surprising that the presence of mannitol in the intragranulate phase of the present invention does not result in tableting trouble, although mannitol is known to be an excipient inducing such troubles. The avoidance of tableting trouble is all the more surprising as it is known in prior art that microcrystalline cellulose, being present in the intragranulate and extragranulate phase, prevents such trouble. However, as could be shown in the present invention, although there is no microcrystalline cellulose present in the intragranulate phase (which was considered as preventing tableting trouble, in combination with microcrystalline cellulose in the extragranulate phase of a pharmaceutical composition), the presence of mannitol does not result in tableting trouble.

Besides the intragranulate phase, the pharmaceutical composition of the present invention further comprises an extragranulate phase. This extragranulate phase comprises microcrystalline cellulose. No microcrystalline cellulose is present in the intragranulate phase. This offers the advantage that the amount of MC used does not have to be split up to two parts, with one part being present in the intragranulate phase and the other part being present in the extragranulate phase. This provides for a simplified process. Further, as MC is not present in the intragranulate phase, it is no part of the granulation process. As the granulation step usually is the step that limits the batch size (due to size constraints of the granulator used), by omitting microcrystalline cellulose in the intragranulate phase the batch size can be increased.

In addition to the MC present, the extragranulate phase may further comprise pharmaceutically acceptable excipients selected from the group consisting of diluents, binders, surfactants, stabilizers, colorants, disintegrants, fluidizers, lubricants, glidants, and pH adjusting agents, wherein preferably the diluent is selected from the group consisting of carbohydrates such as monosaccharides like glucose, oligosaccharides like sucrose and lactose (including anhydrous lactose and lactose monohydrate), starch such as maize starch, potato starch, rice starch and wheat starch, pregelatinized starch, calcium hydrogenphosphate, and sugar alcohols like sorbitol, mannitol, erythritol, and xylitol, a particularly preferred diluent is mannitol;

the binder is selected from the group consisting of hydroxypropylmethylcellulose (HPMC), hydroxypropyl cellulose (HPC), povidone, copovidone (copolymers of vinylpyrrolidone with other vinylderivatives), methylcellulose, powdered acacia, gelatin, gum arabicum, guar gum, carbomer such as carbopol, and polymethacrylates, preferably the binder is hydroxypropyl cellulose or povidone;

the surfactant is selected from the group consisting of sodium lauryl sulfate, polysorbate 80, and polyoxyethylene (160)polyoxypropylene(30)glycol;

the stabilizer is selected from the group consisting of tocopherol, tetrasodium edetate, nicotinamide, and cyclodextrins;

the colorant is selected from the group consisting of food colors such as Food Color Yellow No. 5, Food Color Red No. 2, Food Color Blue No. 2, food lake colors, red ferric oxide, and yellow ferric oxide;

the disintegrant is selected from the group consisting of carmellose (carboxymethyl cellulose), carmellose sodium, carmellose calcium, croscarmellose sodium (cellulose carboxymethylether sodium salt, crosslinked), croscarmellose calcium, starch, sodium starch glycolate, crospovidone (crosslinked polyvinyl pyrrolidone), and low-substituted hydroxypropylcellulose, particularly preferred disintegrants are selected from the group consisting of sodium starch glycolate, crospovidone and croscarmellose sodium, preferably the disintegrant is croscarmellose sodium or crospovidone, more preferably the disintegrant is croscarmellose sodium;

the fluidizer is selected from the group consisting of light anhydrous silicic acid, hydrated silicon dioxide, and talc;

the lubricant is selected from the group consisting of stearic acid, talc, sodium stearyl fumarate and magnesium stearate, a particularly preferred lubricant is magnesium stearate;

the glidant is selected from the group consisting of colloidal silica, hydrophobic colloidal silica and magnesium trisilicate, such as talc, particularly preferred glidants are selected from the group consisting of colloidal silica and hydrophobic colloidal silica; and/or the pH adjusting agent is selected from the group consisting of citrate, phosphate, carbonate, tartrate, fumarate, acetate, and amino acid salts, e.g. the sodium, potassium or calcium salts thereof;

wherein the pharmaceutically acceptable excipients are respectively different from each other. In a further preferred embodiment, the extragranulate phase, in addition to microcrystalline cellulose, only contains a lubricant and a disintegrant as pharmaceutically acceptable excipients, wherein the lubricant and the disintegrant are selected from the respective groups defined above. Particularly preferred, the lubricant is magnesium stearate, and the disintegrant is croscarmellose sodium.

A particular preferred pharmaceutical composition according to the present invention comprises an intragranulate phase and an extragranulate phase, wherein the intragranulate phase, which does not contain microcrystalline cellulose, contains alogliptin or a pharmaceutically acceptable salt thereof as defined above, and as pharmaceutically acceptable excipients, mannitol and HPC, and wherein the extragranulate phase contains, in addition to microcrystalline cellulose, as pharmaceutically acceptable excipients, croscarmellose sodium and magnesium stearate.

A further particular preferred pharmaceutical composition according to the present invention comprises an intragranulate phase and an extragranulate phase, wherein the intragranulate phase does not contain microcrystalline cellulose, but consists of alogliptin or a pharmaceutically acceptable salt thereof as defined above, mannitol and HPC, and wherein the extragranulate phase consists of microcrystalline cellulose, croscarmellose sodium and magnesium stearate.

In a preferred embodiment, the disintegrant of the extragranulate phase of the pharmaceutical composition represents 10 to 90 wt.-%, preferably 20 to 80 wt.-%, more preferably 20 to 40 wt.-% of the pharmaceutically acceptable excipients of the extragranulate phase, the lubricant represents 1 to 15 wt.-%, preferably 2 to 10 wt.-%, more preferably 4 to 8 wt.-% of the pharmaceutically acceptable excipients of the extragranulate phase, and/or the microcrystalline cellulose represents 40 to 90 wt.-%, preferably 55 to 85 wt.-%, more preferably 65 to 75 wt.-% of the pharmaceutically acceptable excipients of the extragranulate phase.

It is possible that in addition to alogliptin or a pharmaceutically acceptable salt thereof as disclosed herein and that is already present in the intragranulate phase, one or more further API(s) or pharmaceutically acceptable salts thereof are present. These additional API(s) is (are) useful in the treatment or prophylaxis of diabetes (such as type 1, type 1.5, or type 2 diabetes, gestational diabetes, diabetes with impaired insulin secretion, obese diabetes, Impaired Glucose Tolerance (IGT), Impaired Fasting Glucose (IFG), Impaired Fasting Glycaemia (IFG)), diabetic complications (e.g. retinopathy, cataract, macroangiopathy, arteriosclerosis, osteopenia, hyperosmolar diabetic coma, infections, diabetic gangrene, xerostomia, hypacusis, cerebrovascular disorder, peripheral blood circulation disorder), hyperlipidemia, or hypertension. Alternatively, the additional API(s)

can be selected from antiobesity agents, diuretics, antithrombotic agents, and the like. In a further preferred embodiment, the further (additional) API is metformin and/or pioglitazone, or pharmaceutically acceptable salts thereof. The preferred salts thereof are metformin hydrochloride and/or pioglitazone hydrochloride.

The further (additional) API(s) can be present in the granulate phase and/or in the extragranulate phase of the pharmaceutical composition/dosage form, and/or in the coating of the dosage form, if such a coating is applied in a later step during the formulation of a dosage form by using the pharmaceutical composition. In which phase (extragranular, intragranular, coating) the additional API most suitably is present, is known to a skilled person and depends on various factors, such as the desired release profile of the further API, manufacturing conditions and limitations, such as possible unwanted interactions between the different API(s) and/or the API(s) and the excipients being present in the different phases. In a preferred embodiment of the present invention, the further (additional) API(s) is (are) present in the intragranulate phase.

In a preferred embodiment, the pharmaceutical composition contains as the only APIs alogliptin monobenzoate in combination with metformin hydrochloride or pioglitazone hydrochloride in the intragranulate phase. The pharmaceutically acceptable excipients are as defined elsewhere herein, preferably the intragranulate phase comprises (preferably consists of) mannitol and HPC, and/or the extragranulate phase comprises (preferably consists of) croscarmellose sodium and magnesium stearate in addition to microcrystalline cellulose.

The extragranulate phase of the pharmaceutical composition of the present invention represents the part of the pharmaceutical composition that is not part of the intragranulate phase. If the pharmaceutical composition has been formulated into a dosage form, the extragranulate phase represents the part of the pharmaceutical composition that is not part of the intragranulate phase, and is not part of the coating that may be present on the dosage form.

The extragranulate phase can be prepared by any suitable method that is known to a person skilled in the art, e.g. by simply mixing the respective ingredients (API(s) if present; excipients). It is also possible that the ingredients of the extragranulate phase are simply mixed with the granules of the intragranulate phase when preparing the pharmaceutical composition. Within the meaning of the present invention, the latter is preferred.

It is also possible that one or more (further) layer(s) and/or coating(s), respectively, are applied on the pharmaceutical composition and dosage form, respectively, according to the present invention. Such layer(s) can for instance be protective layers such as enteric coatings comprising suitable, well known enteric polymers such as polymers that are known to a skilled person from the Eudragit® series. The layer(s)/coating(s) cover(s) the pharmaceutical composition at least partially, preferably completely. In a preferred embodiment, the pharmaceutical composition is coated with a coating comprising hypromellose (hydroxypropyl methyl cellulose); titanium dioxide; and iron oxide (such as iron oxide yellow or iron oxide red). Additionally, the coating may comprise polyethylenglycol (PEG) and/or talc, preferably the coating additionally comprises PEG, more preferably PEG 6000 or PEG 8000, or talc.

The layer(s)/coating(s) can be applied onto the pharmaceutical composition or dosage form by suitable methods that are known to a skilled person. For instance, a film-coating solution or dispersion can be applied (e.g. sprayed) onto a pharmaceutical composition or dosage form by a conventional, suitable film-coating machine. In a preferred embodiment, a water based suspension comprising HPMC, PEG 8000, titanium dioxide and iron oxide is prepared. The tablet cores are coated with this suspension by spraying. Any suitable film coating machine can be used that is known to a skilled person, preferably, the film coating machine "Minicoater" (Glatt corporation/HI coater Lodge corporation) is used.

In a preferred embodiment, the weight percentage of the intragranulate phase is in the range of from 65 to 95 wt.-%, preferably 75 to 85 wt.-%, more preferably 75 to 80 wt.-% based on the combined total weight of the intragranulate phase and extragranulate phase excluding the coating, if present.

The present invention further refers to a pharmaceutical dosage form, comprising or consisting of the pharmaceutical composition as defined elsewhere herein.

Preferably, the pharmaceutical composition according to the present invention is a solid oral dosage form, such as a tablet (including a tablet to be swallowed, an orally disintegrating tablet, an effervescent tablet, a chewable tablet, a lozenge) or a capsule filled with mini-tablets, more preferably the solid oral dosage form is a tablet. This tablet can be coated or uncoated.

The process of formulating the intragranulate and extragranulate phase into the desired dosage form is routine work and can be carried out according to any suitable method that is known to a skilled person. For instance, in order to obtain tablets, the intragranulate phase and the extragranulate phase are mixed and compressed by a single punch machine (stamping press) or by a multi station machine (rotary press). In a preferred embodiment of the present invention, a rotary tableting machine (such as Fette 1200, Fette corporation) is used in order to formulate the intragranulate and extragranulate phase into a tablet. The tableting machine preferably has an oval punch (e.g. 5.5×8.0 mm) to give a tablet (plain or score).

For obtaining capsules filled with mini-tablets, the mini-tablets are produced by compressing the mixture of the intragranulate phase and the extragranulate phase using an equipment suitable for small size tablets, and the thus obtained mini-tablets are then filled into the capsules using standard capsule filling equipment.

The tablet of the present invention can have any suitable form. Preferably, the tablet has an oval, biconvex form. The size of the tablet can be any suitable size, for instance the tablet has a length of 8 to 12 mm, preferably 9 to 11 mm, a width of 4 to 7 mm, preferably 5 to 6 mm, and a height of 3 to 6 mm, preferably 3 to 4 mm.

In a further embodiment, the tablets, preferably in addition to the above-indicated size, exhibit a breaking notch and/or embossment. This breaking notch is then present on one side of the tablet or on both sides of the tablet, preferably on one side of the tablet, and/or said embossment is present on one side of the tablet or on both sides of the tablet, preferably on one side of the tablet.

If such a breaking notch and/or embossment is present, the advantage of the present invention becomes particularly evident: In order to generate tablets exhibiting this particular surface structure, an accordingly formed preforming tool is necessary that exhibits, compared to a preforming tool that is only suitable for generating tablets without said structures, more potential contact (breaking) points. These contact points, in turn, result in inducing tableting trouble in prior art tablets. However, as shown in the present invention, although tablets are prepared that exhibit breaking notch and/or embossment, these tablets do not exhibit tableting trouble during manufacture.

The tablets (in uncoated state) of the present invention exhibit an acceptable tablet hardness, despite having omitted MC in the intragranulate phase.

In a preferred embodiment, the tablets exhibit a hardness in a range of from about 60 to about 150 N, preferably the hardness is in a range of from about 60 to about 120 N, more preferably the hardness is in a range of from about 60 to 100 N, even more preferably the hardness is in a range of from about 70 to 90 N, measured according to the European Pharmacopoeia 5.0, 2.9.8 (resistance to crushing of tablets) with the apparatus Schleuniger Typ 6D 4.11/6D 4.50, wherein the tablets are placed between the jaws in a manner that the force applies to the longest axis of the tablets, where applicable.

The tablets of the present invention exhibit an improved dissolution profile: When the tablets are subjected to a dissolution test according to the Paddle method described in the European Pharmacopoeia 5.0 2.9.3 in a test volume of 900 ml in the test medium 0.01 M HCl at a stirring speed of 50 rpm using a Sotax AP 825 device with a photometer (wavelength 228 nm), not less than 92%, preferably not less than 93%, more preferably not less than 94% of the alogliptin or pharmaceutically acceptable salt thereof is dissolved out in 5 min., and/or not less than 99.5%, preferably not less than 100%, of the alogliptin or pharmaceutically acceptable salt thereof is dissolved out in 10 min.

Further, the present invention refers to a process for preparing a pharmaceutical composition comprising an intragranulate phase and an extragranulate phase, comprising the steps of (a) providing an intragranulate phase comprising one or more pharmaceutically active ingredient(s), wherein one pharmaceutically active ingredient is 2-({6-[(3R)-3-aminopiperidin-1-yl]-3-methyl-2,4-dioxo-3,4-dihydropyrimidin-1(2H)-yl}methyl)benzonitrile (alogliptin) or a pharmaceutically acceptable salt thereof, and wherein said intragranulate phase is free from microcrystalline cellulose;

(b) providing an extragranulate phase comprising microcrystalline cellulose, preferably the extragranulate phase is added to the granulate obtained after step (a);

(c) mixing the intragranulate phase from step (a) with the extragranulate phase from step (b) in order to obtain a pharmaceutical composition comprising an intragranulate phase and an extragranulate phase.

With regard to the expressions "intragranulate phase", "extragranulate phase", "alogliptin or a pharmaceutically acceptable salt thereof", and further expressions and process steps, in particular the process steps applied for the manufacture of the granulate phase and the extragranulate phase, reference is made to the disclosure elsewhere herein.

The intragranulate phase can further comprise one or more pharmaceutically acceptable excipients, selected from the group as defined elsewhere herein, and wherein said pharmaceutically acceptable excipients are not microcrystalline cellulose.

Step (a), i.e. the provision of an intragranulate phase comprising one or more pharmaceutically active ingredient(s), wherein one pharmaceutically active ingredient is 2-({6-[(3R)-3-aminopiperidin-1-yl]-3-methyl-2,4-dioxo-3,4-dihydropyrimidin-1(2H)-yl}methyl)benzonitrile (alogliptin) or a pharmaceutically acceptable salt thereof, being free form MC, comprises a wet granulation step or a dry granulation step, preferably a wet granulation step, more preferably a fluidized bed granulation step. In particular if a granulation step is applied, the batch size of the tablets prepared is limited by technical constraints, e.g. the respective equipment size of the granulator used. By avoiding the splitting of the amount of MC used, i.e. by omitting MC in the intragranulate phase, the batch size can be increased as greater amounts of the further components can be used instead of MC.

In a further preferred embodiment, step (a) comprises (a-1) uniformly mixing the one or more pharmaceutically active ingredient(s) and, if present, the one or more pharmaceutically acceptable excipient(s), thereby obtaining a mixture, and (a-2) granulating the mixture obtained in step (a-1), preferably by using an aqueous granulation liquid, more preferably by spraying an aqueous solution of hydroxypropylcellulose, thereby obtaining a granulate, (a-3) drying the granulate obtained in step (a-2), and (a-4) pulverizing the granulate and sieving the pulverized granulate, thereby obtaining sized granulate. This granulate will form the intragranulate phase, when combined with the extragranulate phase.

The granulation step (a-2) can be carried out according to suitable protocols respectively adapted to the apparatus that is used. For instance, if the granulation step (a-2) is carried out by using a fluidized bed granulation dryer (e.g. GPCG, Glatt corporation), then the inlet air temperature used is in the range of from 50-100° C., preferably 60-70° C.; the outlet air temperature is in the range of from 20-40° C., preferably 30-40° C., and the product temperature is in the range of from 20-35° C., preferably 22-28° C. The respective suitable apparatus, e.g. fluidized bed granulation dryer, is known to a person skilled in the art.

The extragranulate phase of step (b), in addition to the microcrystalline cellulose, can further comprise pharmaceutically acceptable excipients as defined elsewhere in the present invention.

The mixing of the granulate phase with the extragranulate phase (step (c)) can be carried out according to any suitable method that is known to a person skilled in the art. For instance, the ingredients of the extragranulate phase can be pre-mixed and only then added to/mixed with the intragranulate phase, or the ingredients of the extragranulate phase can be added directly to the intragranulate phase, without preceding pre-mixing of its ingredients. In a preferred embodiment, the ingredients forming the extragranulate phase are directly added to the intragranulate phase.

In a preferred embodiment, mixing step (c) is carried out over a time period being in the range of from about 5 min. to 30 min., preferably from about 10 min. to 20 min.

The process for preparing a pharmaceutical composition optionally comprises an additional step (d), which is a step of formulating the pharmaceutical composition into a dosage form, preferably into a solid oral dosage form such as a tablet (including a tablet to be swallowed, an orally disintegrating tablet, an effervescent tablet, a chewable tablet, a lozenge) or a capsule filled with mini-tablets, preferably a tablet. The step of formulating the pharmaceutical composition into a dosage form can be carried out by applying any suitable process. Preferably, this step involves the use of a compression step, however no granulation step such as wet or dry granulation is applied. An example of how such a formulation step can be carried out is disclosed above.

The present invention further refers to a granulate comprising one or more pharmaceutically active ingredients, wherein one pharmaceutically active ingredient is 2-({6-[(3R)-3-aminopiperidin-1-yl]-3-methyl-2,4-dioxo-3,4-dihydropyrimidin-1(2H)-yl}methyl)benzonitrile (alogliptin) or a pharmaceutically acceptable salt thereof, and wherein said granule is free from microcrystalline cellulose. As disclosed elsewhere herein, the intragranulate phase of the pharmaceutical composition of the present invention comprises multiple granules. Thus, the granulate of the present invention can be used for preparing a pharmaceutical composition as disclosed elsewhere herein. Then, this granulate is referred to as "intragranular phase". As the granulate is free from MC, its preparation is more simple and less cost-intensive compared to the preparation of prior art granulates. Whether or not MC is present can be determined according to any suitable method that is known to a person skilled in the art, e.g. by visual inspection (electron microscope).

In a preferred embodiment, the amount of alogliptin or its pharmaceutically acceptable salt in the granulate is in the range of from 3 to 50 wt.-%, preferably 5 to 35 wt.-%, more preferably 7 to 30 wt.-%, based on the total amount of ingredients of the granulate. The alogliptin or its pharmaceutically acceptable salt are as defined elsewhere in the present invention.

It is also possible that the granulate according to the present invention further comprises metformin and/or pioglitazone as API, or pharmaceutically acceptable salts thereof. Preferably, such salts are metformin hydrochloride and/or pioglitazone hydrochloride.

The excipients that can be comprised in the granulate according to the present invention are as described elsewhere herein with regard to "intragranulate phase".

The present invention further refers to a process for preparing a granulate as described herein, wherein said process comprises a granulation step. With regard to said granulation step, reference is made to the disclosure above.

The present invention further refers to an intragranulate phase comprising the granulate as described herein.

Additionally, the present invention refers to a pharmaceutical composition as disclosed herein, a pharmaceutical dosage form as disclosed herein, a tablet as disclosed herein, or a granulate as disclosed herein, for use in a method of treating diabetes, preferably type 2 diabetes.

Finally, the present invention refers to a pharmaceutical composition obtained by applying a process as disclosed herein, preferably wherein this pharmaceutical composition is a solid oral dosage form, such as a tablet (including a tablet to be swallowed, an orally disintegrating tablet, an effervescent tablet, a chewable tablet, a lozenge) or a capsule filled with mini-tablets, preferably said solid oral dosage form is a tablet.

The pharmaceutical composition obtained by applying a process as disclosed herein exhibits improved properties e.g. with regard to tablet hardness, content uniformity and/or dissolution profile when compared to the respective properties of pharmaceutical compositions obtained by applying prior art processes. The respective properties are measured by respectively applying the same tests, preferably the tests as disclosed herein (content uniformity: European Pharmacopoeia 8.0 2.9.40; dissolution test for solid dosage forms: European Pharmacopoeia 5.0 2.9.3; Resistance to crushing of tablets (tablet hardness): European Pharmacopoeia, 5.0 2.9.8).

By applying electrone microscopy or Raman spectroscopy, it can be measured/verified in the (final) product (e.g. tablet) whether MC is present in the intragranulate or extragranulate phase, in particular whether the intragranulate phase is really free from MC. Further, by applying these methods, the amount of MC being present in the extragranulate phase can be determined.

DESCRIPTION OF THE FIGURES

FIG. 1 depicts the dissolution profile of the tablets according to Example 2.

FIG. 2 depicts the dissolution profile of the tablets according to Example 3.

Figure 3A:
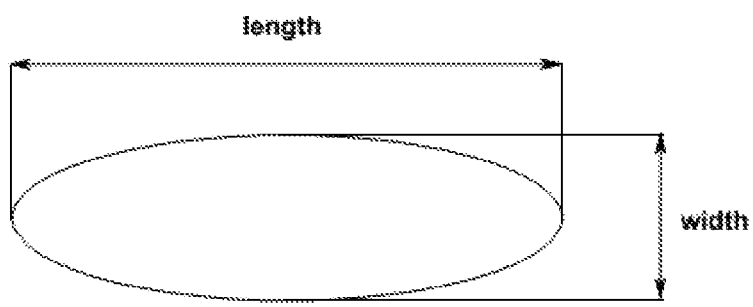
FIG. 3a) shows the length and the width of the oval biconvex tablet (top view), and FIG. 3b) shows the height of the oval biconvex tablet (side view).
Figure 3B:
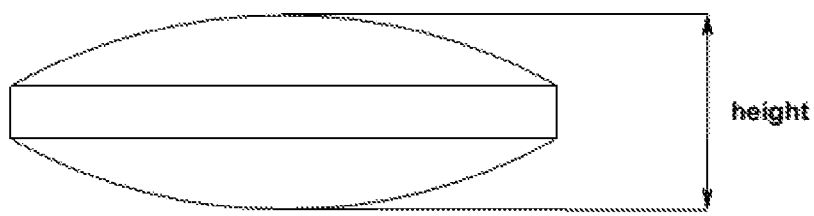
FIG. 3 is a scheme of a tablet having an oval biconvex form.

From FIGS. 1 and 2 it can be seen that the tablet comprising microcrystalline cellulose only in the extragranulate phase (FIG. 2) exhibits an improved dissolution profile compared to the dissolution profile of a tablet comprising microcrystalline cellulose in both, the intragranulate phase and in the extragranulate phase (FIG. 1).

The tablets used for analysis were prepared as described in the "Examples" section below.

The following examples illustrate the process of the present invention and are not intended to limit the scope of the invention set forth in the claims appended hereto.

EXAMPLES

1. Tablets Prepared

1.1 Example 1

| | Amount |
|---|---|
| Components of the intragranulate phase | |
| Alogliptin monobenzoate (form A) | 8.50 mg/tablet |
| Microcrystalline cellulose | 22.50 mg/tablet |
| Mannitol | 105.20 mg/tablet |
| Hydroxypropylcellulose | 4.50 mg/tablet |
| Components of the extragranulate phase | |
| Croscarmellose sodium | 7.50 mg/tablet |
| Magnesium stearate | 1.80 mg/tablet |
| Sum | 150.00 mg/tablet |

1.2 Example 2

| | Amount |
|---|---|
| Components of the intragranulate phase | |
| Alogliptin monobenzoate (form A) | 8.50 mg/tablet |
| Microcrystalline cellulose | 15.00 mg/tablet |
| Mannitol | 105.20 mg/tablet |
| Hydroxypropylcellulose | 4.50 mg/tablet |
| Components of the extragranulate phase | |
| Croscarmellose sodium | 7.50 mg/tablet |
| Magnesium stearate | 1.80 mg/tablet |
| Microcrystalline cellulose | 7.50 mg/tablet |
| Sum | 150.00 mg/tablet |

1.3 Example 3

| | Amount |
|---|---|
| Components of the intragranulate phase | |
| Alogliptin monobenzoate (form A) | 8.50 mg/tablet |
| Mannitol | 105.20 mg/tablet |
| Hydroxypropylcellulose | 4.50 mg/tablet |
| Components of the extragranulate phase | |
| Croscarmellose sodium | 7.50 mg/tablet |
| Magnesium stearate | 1.80 mg/tablet |
| Microcrystalline cellulose | 22.50 mg/tablet |
| Sum | 150.00 mg/tablet |

1.4 Manufacturing Procedure for all Three Examples

The components of the intragranulate phase as listed above were uniformly mixed in a fluidized bed granulation dryer (GPCG, Glatt corporation), the mixture was granulated by spraying an aqueous solution of hydroxypropylcellulose and dried therein.

The obtained intragranulate phase (granulate; granules) was pulverized and sieved through a 1.0 mm sieve. To the obtained sized granules the components of the extragranulate phase as listed above were added and mixed in a tumbler mixer (Turbola® mixer, Bachofen AG) to give a mixture for tableting.

The mixture for tableting was punched by a rotary tableting machine (Fette 1200, Fette corporation) with an oval punch (5.5×8.0 mm) to give tablets having a breaking notch on one side.

The tablets of Examples 1, 2 and 3 were prepared uncoated. The tablets of Examples 2 and 3 were additionally coated according to the procedure described below (1.5).

1.5 Coating

Coating Suspension, Ingredients:

| Component | Amount (mg/tablet) |
|---|---|
| HPMC (hydroxypropylmethylcellulose) | 5.39 |
| polyethylene glycol (PEG 6000) | 0.09 |
| titanium dioxide | 0.61 |
| iron oxide red | 0.01 |
| Sum | 6.10 mg/tablet |

A water based suspension is prepared. The tablet cores (intragranulate and extragranulate phase, tableted as described above in 1.4) are coated with this suspension by spraying them. This is carried out with a film coating machine (Minicoater, Glatt corporation/HI coater Lodge corporation).

However, for the following tests, only uncoated tablets of Examples 1, 2, and 3 (item 1.1, 1.2, 1.3 above) were used.

2. Tests Carried Out

2.1 Assessing Occurrence of Tableting Trouble

Tablets of Example 1:
The mixture for tableting (comprising the intragranulate phase and the extragranulate phase) showed shortly after (within a time period of 2 min.) the start of the tableting process severe tableting trouble (sticking to the punch and capping).

Tablets of Example 2:
The mixture for tableting (comprising the intragranulate phase and the extragranulate phase) showed after a while (after more than 2 min., and up to 10 min.) the start of the tableting process tableting trouble (sticking to the punch and capping).

Tablets of Example 3:
The mixture for tableting (comprising the intragranulate phase and the extragranulate phase) showed no tableting trouble during the whole tableting process (in particular no sticking to the punch and capping).

2.2 Assessing Dissolution Properties

In order to assess the influence of the compositions of the intragranular phase and the extragranular phase to the product (tablet) properties, dissolution tests were carried out.

The dissolution properties of the tablets of Examples 2 and 3 (no suitable tablets could be produced according to Example 1) were measured according to the Paddle method described in the European Pharmacopoeia 5.0 2.9.3 in a test volume of 900 ml in the test medium 0.01 M HCl at a stirring speed of 50 rpm using a Sotax AP 825 device with a photometer (wavelength 228 nm).

The respective values obtained represent the mean value of six different measurements.

Example 2

| Time [min] | Dissolution [%] |
|---|---|
| 0 | 0.0 |
| 5 | 91 |
| 10 | 99 |
| 15 | 99 |
| 20 | 99 |
| 30 | 99 |
| 45 | 99 |
| 60 | 99 |

The respective graph is depicted in FIG. 1.

As can be seen, within 5 minutes after start, 91% of the API (alogliptin monobenzoate) is dissolved. After 10 minutes, 99% are dissolved.

Example 3

| Time [min] | Dissolution [%] |
|---|---|
| 0 | 0.0 |
| 5 | 94 |
| 10 | 100 |
| 15 | 100 |
| 20 | 100 |
| 30 | 100 |
| 45 | 100 |
| 60 | 100 |

The respective graph is depicted in FIG. 2.

As can be seen, within 5 minutes after start, 94% of the API (alogliptin monobenzoate) is dissolved. After 10 minutes, 100% are dissolved.

2.3 Assessing Content Uniformity

In order to assess the influence of the compositions of the intragranular phase and the extragranular phase to the product (tablet) properties, content uniformity tests were carried out.

The content uniformity of the tablets of Examples 2 and 3 (no suitable tablets could be produced according to Example 1) was measured according to the method described in the European Pharmacopoeia 8.0 2.9.40. The number of samples is 10, respectively. The results were as follows:

Example 2

Acceptance value: 5.2

Example 3

Acceptance value: 4.4

From these results it can be seen that the content uniformity of the tablets of Example 3 is improved compared to the content uniformity of the tablets of Example 2.

The invention claimed is:

1. A pharmaceutical composition comprising an intragranulate phase and an extragranulate phase, wherein
   (i) said intragranulate phase comprises one or more pharmaceutically active ingredient(s);
   (ii) one pharmaceutically active ingredient in the intragranulate phase is 2-({6-[(3R)-3-aminopiperidin-1-yl]-3-methyl-2,4-dioxo-3,4-dihydropyrimidin-1(2H)-yl}methyl)benzonitrile (alogliptin) or a pharmaceutically acceptable salt thereof;
   (iii) said intragranulate phase is free from microcrystalline cellulose;
   (iv) said extragranulate phase comprises microcrystalline cellulose;
   (v) said extragranulate phase, in addition to microcrystalline cellulose, only contains a lubricant and a disintegrant as pharmaceutically acceptable excipients;
   (vi) said intragranulate phase contains, as pharmaceutically acceptable excipients, mannitol and hydroxypropyl cellulose (HPC);
   (vii) said extragranulate phase contains, in addition to microcrystalline cellulose, as pharmaceutically acceptable excipients, croscarmellose sodium and magnesium stearate; and
   (viii) said intragranulate phase does not contain a disintegrant.

2. The pharmaceutical composition according to claim 1, wherein the alogliptin or a pharmaceutically acceptable salt thereof is alogliptin monobenzoate or alogliptin free base, and wherein the alogliptin monobenzoate is in the form of polymorphic form A or in amorphous form, and wherein the alogliptin free base is in the form of polymorphic form B, wherein said polymorphic form A is characterized by one or more physical properties selected from the group consisting of:
   an X-ray powder diffraction pattern using Cu-Kα radiation with diffraction peaks at positions (° 2Θ) as follows: 9.44, 10.84, 17.82, 18.75, 25.87, 28.52, with +/−0.2 tolerance range of the respective 2Θ value;
   an IR spectrum comprising absorption peaks at 1212, 1365, 1447, 1613 and 1697 cm$^{-1}$, with +/−2 cm$^{-1}$ tolerance range of the respective value;
   an FT-Raman spectrum comprising peaks at 1065, 1103, 1235, 1288, 1337, 1365, 1624, 1689, 2883, 2983 and 3026 cm$^{-1}$ with +/−2 cm$^{-1}$ tolerance range of the respective value; and
   a differential scanning calorimetry spectrum having an endotherm range at about 173° C. to about 195° C.; and wherein said amorphous form is characterized by one or more physical properties selected from the group consisting of:
   an X-ray powder diffraction pattern that shows a broad halo with no specific peaks present using Cu-Kα radiation;
   an IR spectrum comprising absorption peaks at 1703, 1599, 1119, 868 and 809 cm$^{-1}$;
   an FT-Raman spectrum comprising peaks at 805, 1280 and 1703 cm$^{-1}$; and
   a differential scanning calorimetry spectrum having a $T_g$=70° C. (onset), an exotherm at 132° C., and an endotherm onset at 183° C.; and wherein said polymorphic form B is characterized by one or more physical properties selected from the group consisting of:
   an X-ray powder diffraction pattern using Cu-Kα radiation with diffraction peaks at positions (° 2Θ) as follows: 10.9, 12.5, 18.0, 19.0, 21.8, with +/−0.2 tolerance range of the respective 2Θ value; an IR spectrum comprising absorption peaks at 3358.7, 2223.7, 1642.2, 1433.4, 818.4 and 771.2 cm$^{-1}$, with +/−2 cm$^{-1}$ tolerance range of the respective value.

3. The pharmaceutical composition according to claim 1, wherein the intragranulate phase further comprises one or more pharmaceutically acceptable excipients, selected from the group consisting of binders, diluents, surfactants, stabilizers, colorants, fluidizers, and pH adjusting agents, wherein said pharmaceutically acceptable excipients are not microcrystalline cellulose, and wherein the pharmaceutically acceptable excipients are respectively different from each other, if the intraganulate phase comprises more than one excipient.

4. The pharmaceutical composition according to claim 1, wherein the intragranulate phase in addition to the pharmaceutically active ingredient only comprises, as pharmaceutically acceptable excipient, a binder and/or a diluent.

5. The pharmaceutical composition according to claim 1, wherein the extragranulate phase further comprises, in addition to the microcrystalline cellulose, pharmaceutically acceptable excipients selected from the group consisting of diluents, binders, surfactants, stabilizers, colorants, disintegrants, fluidizers, lubricants, glidants, and pH adjusting agents, wherein the pharmaceutically acceptable excipients are respectively different from each other.

6. The pharmaceutical composition according to claim 1, wherein at least one further pharmaceutically active ingredient (API) or pharmaceutically acceptable salt thereof, in addition to alogliptin or its pharmaceutically acceptable salt, is present.

7. The pharmaceutical composition according to claim 6, wherein the only pharmaceutically active ingredients being present in the pharmaceutical composition are
   alogliptin monobenzoate; and
   metformin hydrochloride or pioglitazone hydrochloride.

8. The pharmaceutical composition according to claim 1, wherein said pharmaceutical composition comprises a coating.

9. A pharmaceutical dosage form comprising or consisting of the pharmaceutical composition as defined in claim 1.

* * * * *